US012745947B2

(12) United States Patent
Doidge et al.

(10) Patent No.: US 12,745,947 B2
(45) Date of Patent: Sep. 29, 2026

(54) EVALUATION OF PAIN DISORDERS VIA EXPERT SYSTEM

(71) Applicant: CEREBRAL DIAGNOSTICS CANADA INCORPORATED, Toronto (CA)

(72) Inventors: Mark S. Doidge, Toronto (CA); Mario Garingo, Toronto (CA)

(73) Assignee: CEREBRAL DIAGNOSTICS CANADA INCORPORATED, Toronto (CA)

( * ) Notice: Subject to any disclaimer, the term of this patent is extended or adjusted under 35 U.S.C. 154(b) by 820 days.

(21) Appl. No.: 17/599,691

(22) PCT Filed: Apr. 2, 2020

(86) PCT No.: PCT/IB2020/053117

§ 371 (c)(1),
(2) Date: Sep. 29, 2021

(87) PCT Pub. No.: WO2020/202045

PCT Pub. Date: Oct. 8, 2020

(65) Prior Publication Data

US 2022/0192578 A1 Jun. 23, 2022

Related U.S. Application Data

(60) Provisional application No. 62/828,013, filed on Apr. 2, 2019.

(51) Int. Cl.
*A61B 5/383* (2021.01)
*A61B 5/00* (2006.01)
(Continued)

(52) U.S. Cl.
CPC ............ *A61B 5/383* (2021.01); *A61B 5/4824* (2013.01); *A61B 5/4833* (2013.01);
(Continued)

(58) Field of Classification Search
CPC ....... A61B 5/383; A61B 5/377; A61B 5/4824; A61B 5/4833; A61B 5/7257; A61B 5/726;
(Continued)

(56) References Cited

U.S. PATENT DOCUMENTS 5,406,956 A * 4/1995 Farwell .................. A61B 5/377 600/544
2012/0123232 A1 5/2012 Najarian et al.
(Continued)

FOREIGN PATENT DOCUMENTS

CN 108320800 A * 7/2018 ......... G06K 9/00523
WO 2019009420 A1 1/2019

OTHER PUBLICATIONS

Applicant: Cerebral Diagnostics Canada Incorporated; "Diagnosis of Pain Disorder via Expert System"; PCT International Application No. PCT/IB2020/053117 Filed: Apr. 20, 2020; PCT International Search Report and Written Opinion; Jun. 23, 2020; 11 Pgs.
(Continued)

*Primary Examiner* — Jeffrey G. Hoekstra
(74) *Attorney, Agent, or Firm* — Tarolli, Sundheim, Covell & Tummino LLP

(57) ABSTRACT

Systems and methods are provided for evaluating a pain disorder. A stimulus is applied to a subject and an evoked potential is obtained from at least one electrogram of the subject. A set of features is extracted from the evoked potential including features from at least two of a set of features representing connectivity between regions of the brain, a set of morphology features, a set of features representing time and frequency, a set of signal decomposition features, and a set of features representing entropy. A clinical
(Continued)

parameter relating to a pain disorder is assigned to the subject from the extracted set of features with a machine learning model.

16 Claims, 3 Drawing Sheets

(51) Int. Cl.
*A61B 5/369* (2021.01)
*G06N 20/00* (2019.01)

(52) U.S. Cl.
CPC ............ *A61B 5/7257* (2013.01); *A61B 5/726* (2013.01); *G06N 20/00* (2019.01); *A61B 5/369* (2021.01); *A61B 5/7264* (2013.01)

(58) Field of Classification Search
CPC ....... A61B 5/369; A61B 5/374; A61B 5/7264; A61B 5/4836; G06N 20/00; G06N 20/10; G06N 20/20; G06N 5/01; G16H 20/70; G16H 20/10; G16H 50/20; G16H 50/70
See application file for complete search history.

(56) References Cited

U.S. PATENT DOCUMENTS

| | | | | |
|---|---|---|---|---|
| 2014/0324118 | A1 | 10/2014 | Simon et al. | |
| 2018/0085584 | A1 * | 3/2018 | Thakur | A61B 5/4824 |
| 2018/0093092 | A1 | 4/2018 | Howard | |
| 2019/0091403 | A1 * | 3/2019 | Osorio | A61M 5/1723 |
| 2022/0004913 | A1 * | 1/2022 | Nakae | G06N 20/20 |

OTHER PUBLICATIONS

Graversen, C., et al.; "Biomarkers for visceral hypersensitivity identified by classification of electroencephalographic frequency alterations"; Journal of Neural Engineering, 8(5), 056014; Sep. 15, 2011; 10 pgs. doi:10.1088/1741-2560/8/5/056014.

Applicant: Cerebral Diagnostics Canada Incorporated; "Evaluation of Pain Disorders Via Expert System"; Canadian Patent Application No. 3,135,329; Canadian Office Action; Feb. 27, 2024; 6 pgs.

Applicant: Cerebral Diagnostics Canada Incorporated; "Evaluation of Pain Disorders Via Expert System"; Canadian Patent Application No. 3,135,329; Canadian Examination Report; Dec. 23, 2022; 7 pgs.

Japanese Patent application 2021-560330; Japanese Office Action dated Nov. 19, 2024; 5 Pgs.

* cited by examiner

EVALUATION OF PAIN DISORDERS VIA EXPERT SYSTEM

CROSS-REFERENCE TO RELATED APPLICATION

This patent application is a U.S. National Stage Application filed under 35 U.S.C. § 371 of PCT/IB2020/053117, filed Apr. 2, 2020, and entitled EVALUATION OF PAIN DISORDERS VIA EXPERT SYSTEM, which International Application claims the benefit of priority from U.S. Provisional Patent Application No. 62/828,013, filed on Apr. 2, 2019. The entire contents of each of the above-identified patent applications are incorporated herein by reference.

TECHNICAL FIELD

This invention relates to diagnosis of pain conditions and disorders via expert systems.

BACKGROUND

Measuring pain experienced by a subject is difficult, and is currently limited, for the most part, to observation of the subject's behavior and self-reporting. However, since both observation and self-reporting are subjective, making an objective measure of experienced pain or an increase in pain in response to a stimulus difficult to measure. Unfortunately, a number of disorders present with pain as a primary symptom, and therefore, the inability of caregivers to objectively measure the subject's pain levels, and in particular, a change in pain level in response to stimuli, can complicate diagnosis of these conditions and disorders.

For example, neuropathic pain is pain caused by damage or disease affecting the somatosensory nervous system. Neuropathic pain may be associated with abnormal sensations (paraesthesia and dysesthesia) and/or pain from normally non-painful stimuli (allodynia), and/or increased pain from normally painful stimuli (hyperalgesia) that may be continuous and/or appear episodically. Central neuropathic pain may be an outcome of spinal cord injury, multiple sclerosis, and strokes in some parts of the central nervous system. Along with diabetes and other metabolic conditions, common causes of painful peripheral neuropathies include nutritional deficiencies, toxins, certain viral and bacterial diseases, remote manifestations of malignancies, immune mediated disorders, physical trauma to a nerve trunk trunk, or other tissues such as muscles, joints, bone, and teeth. Fibromyalgia (FM) is characterized by widespread chronic pain and tenderness, psychological distress, and fatigue. Fibromyalgia is considered to be one type of what are referred to as "mechanical pain disorders". Other mechanical pain disorders are believed to include: temporo-mandibular joint disorder, chronic fatigue syndrome, myofascial pain syndrome, chronic widespread pain, gulf war syndrome, complex regional pain syndrome, some types of post-traumatic stress disorder, some cases of low back pain, some types of vulvar vestibulitis/vulvodynia, and *piriformis* muscle syndrome. Current knowledge about the pathophysiology of FM is limited but neuro-imaging studies have revealed brain responses to experimental pain stimulations in subjects. This has led to the currently held dogma that FM, and possibly other mechanical pain disorders, may be due to central sensitization of pain processing.

SUMMARY

In one example, a method includes applying a stimulus to a subject and obtaining an evoked potential from at least one electrogram of the subject. A set of features is extracted from the evoked potential including features from at least two of a set of features representing connectivity between regions of the brain, a set of morphology features, a set of features representing time and frequency, a set of signal decomposition features, and a set of features representing entropy. A clinical parameter relating to a pain disorder is assigned to the subject from the extracted set of features with a machine learning model.

In another example, a system includes an electrogram interface that receives a recorded evoked potential from an electrogram of a subject. A feature extractor extracts a set of features from the evoked potential including features from at least two of a set of features representing connectivity between regions of the brain, a set of morphology features, a set of features representing time and frequency, a set of signal decomposition features, and a set of features representing entropy. A machine learning model that assigns a clinical parameter relating to a pain disorder to the subject from the extracted set of features.

In a further example, a method includes applying a stimulus to a subject and obtaining an evoked potential from at least one electroencephalogram (EEG) of the subject. Each of a set of features representing connectivity between regions of the brain are extracted, a set of morphology features, a set of coefficients from one of a discrete Fourier transform, autoregressive methods, and a continuous wavelet transform, a set of signal decomposition features, and a set of features representing entropy are extracted from the evoked potential. The extracted features are then combined to provide a set of composite features. It is determined with a machine learning model if the subject is likely to benefit from a treatment to a pain disorder from the set of composite features. Treatment is provided to the subject if it is determined that the treatment is likely to be effective.

DETAILED DESCRIPTION

A "pain disorder," as used herein, refers to any condition in which pain is a primary symptom, including, but not limited to, somatoform disorders, neuropathic disorders, and chronic pain for which the cause is unknown. The pain disorders evaluated by the systems and methods included herein can include pain caused by: peripheral mechanisms (e.g., inflammatory, nociceptive, neurogenic, traumatic, or metabolic), or central mechanisms (e.g., without any known organic bodily trigger), as well as pain that manifests acutely, subacutely, and/or chronically (i.e., as persistent pain lasting more than 6 months) and manifests as neuropathic pain.

A "subject", as used herein, is a human being that is either receiving medical evaluation and care from a medical professional or a participant in a research project.

Objective measurement of the pain experienced by another human being is difficult, particularly when there is no apparent physiological cause for the pain. As a result, medical professionals are often forced to rely on subjective reporting in diagnosing and monitoring patients under their care or subjects in a research trial. Worse yet, subjects may not be able to articulate the type of pain they are feeling or various pain phenomena that they may experience clearly complicating diagnosis and treatment. The systems and methods described here utilize combinations of features extracted from a potential evoked in response to a stimulus to evaluate one or more of the presence, nature, cause, and severity of pain experienced by a patient. By combining features obtained through multiple, distinct analyses of the evoked potential, each of the presence, nature, cause, and severity of pain can be accurately determined, allowing for insight into the pain experienced by the patient.

Figure 1:
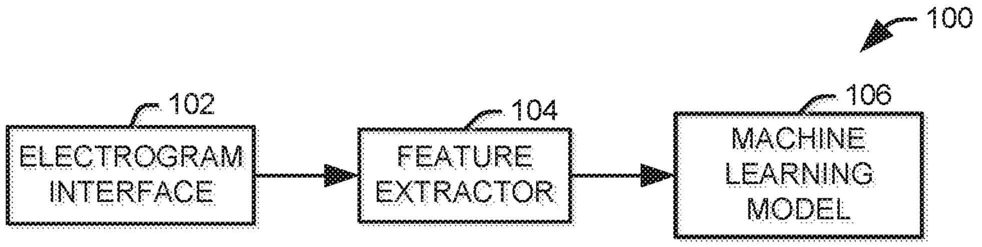
FIG. 1 illustrates a system for determining if a subject suffers from a pain disorder.

FIG. 1 illustrates one example of a system 100 for evaluating a subject in accordance with an aspect of the present invention. In one implementation, the system is implemented as computer readable instructions, executed by a processor and stored on a non-transitory computer readable medium. The system 100 includes an electrogram interface 102 that receives electrogram data for the subject from a set of electrodes (not shown) and formats the data in an appropriate form for used by the system 100. In practice, the electrogram data is recorded after a stimulus is applied to the subject to provide an evoked potential. As used herein, an "evoked potential" is intended to refer to either of the results of a single electrogram following introduction of a stimulus or an isolated event related potential from multiple electrograms.

A feature extractor 104 extracts parameters from the evoked potential. Specifically, the feature extractor extracts parameters that are relevant to distinguishing between subjects with pain disorders and subjects who do not have pain disorders, referred to herein as "features". Exemplary features can include various parameters from each of five categories, a first including parameters representing the morphology of selected waveforms within the electrogram data, a second using coefficients from a signal decomposition of the electrogram data, a third including one or more entropy measures for the electrogram data, a fourth including parameters representing time and frequency characteristics of the signal, and a fifth including parameters representing connectivity between various regions of the brain. In the illustrated example, the feature extractor 104 extracts features from at least two of these categories, although it will be appreciated that, in some implementations, features from three, four, or all of the categories can be used.

A machine learning model 106 uses the plurality of extracted features to assign a clinical parameter to the subject. The machine learning model 106 can utilize one or more classification or regression algorithms, each of which analyze the extracted features or a subset of the extracted features to assign a continuous or categorical parameter relating to a pain disorder and provide this information to a user via an appropriate output device, such as a display. The clinical parameter can represent any of: 1.) the presence of a pain disorder generally; 2.) the presence of a specific pain disorder (e.g., fibromyalgia); 3.) a predicted or actual response to treatment for a pain disorder; 4.), a presence or absence of a given tender spot; 5.) a type of pain; 6.) a subtype of a pain disorder; 7.) a severity of pain; 8.) severity of a pain disorder; 9.)_a change in the severity of a pain disorder over time; 10.) the presence of absence of a particular pain phenomena (e.g., central sensitization, hyperalgesia, allodynia and hypoalgesia), 11.) an intensity of a particular pain phenomena; 12.) a likelihood that the subject suffers from a pain disorder generally; 13.) a likelihood that the subject suffers from a specific pain disorder; 14.) a symptom of a pain disorder, or 15.) a finding on a physical exam. In the illustrated implementation, the machine learning model 106 includes one or both of a support vector machine and a random forest classifier.

Figure 2:
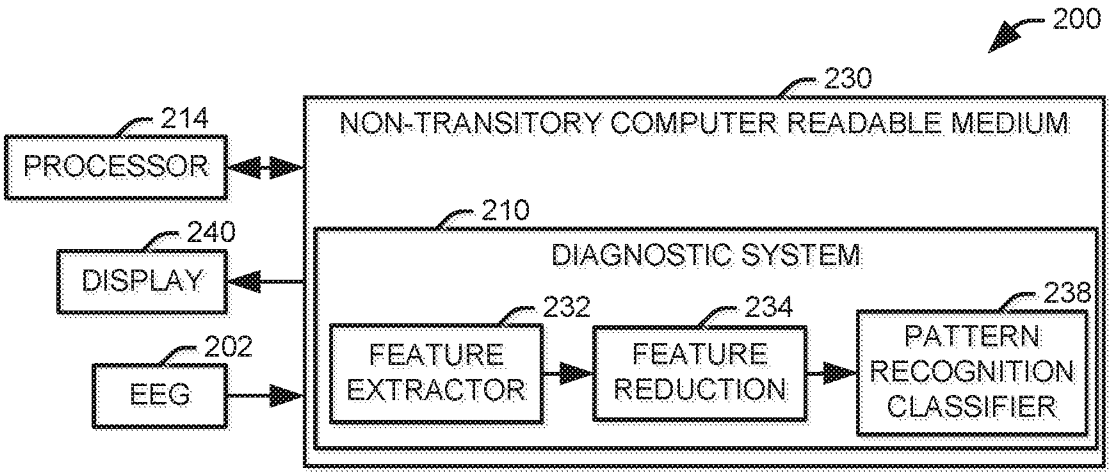
FIG. 2 illustrates one example of a system for evaluating a subject for a pain disorder.

FIG. 2 illustrates one example of a system 200 for evaluating a subject for in accordance with an aspect of the present invention. An electroencephalograph (EEG) device 202 can be used to record electroencephalogram data from the subject. This data is provided to a pain evaluation system 210 implemented as computer readable instructions, executed by a processor 214 and stored on a non-transitory computer readable medium 230. The pain evaluation system 210 includes a feature extractor 232 that extracts a vector of feature values from the electroencephalogram data. Exemplary features can include various parameters representing morphology of selected waveforms within the electroencephalogram data, a signal decomposition of the electroencephalogram data, one or more entropy measures for the electroencephalogram data, parameters representing time and frequency characteristics of the signal, and parameters representing connectivity between various regions of the brain. In the illustrated example, the feature extractor 232 extracts a significant number of features from these categories and utilizes composite features generated via a feature reduction process 234 to generate a set of composite features for consideration.

In one implementation, the feature extractor 232 can extract features from an individual EEG taken in response to a stimulus applied to a subject. The stimulus can include, for example, any of heat, cold, mechanical pressure, electrical stimulation, and laser stimulation applied to a selected location on the body of the subject. In one example, a mechanical force can be applied to one of the tender spots identified on the subject or one or more of a standard list of tender spots associated with fibromyalgia. This mechanical force can be applied manually or with a mechanical device to standardize the applied force. In one implementation, stimulations were applied with a force equivalent to two kilograms at a speed of two hundred millimeters per second with a rubber stopper having a surface area of one square centimeter. In another implementation, multiple EEGs can be taken after respective stimulations and features can be extracted from an average taken across the EEG signals to remove background noise and isolate an event related potential. In one example, stimulation is applied thirty times to the selected location with an interstitials interval of ten to fourteen seconds, and the event related potential is generated as a Woody Filter Mean. In another implementation, the intensity of the stimulus can be incrementally increased until the subject reports that they are experiencing pain, with the evoked potential obtained only after the stimulus is of sufficient intensity to evoke a pain response.

Parameters representing morphology of a selected waveform within the EEG data can include any parameter describing a shape of a detected waveform. Extracted features can include the amplitude or width of an N1 peak, an amplitude and width of a P1 trough, a peak to peak voltage, and a duration of the event related potential. Parameters representing entropy that can be calculated from a waveform or an event related potential can include the Petrosian Fractal Dimension (PFD), the Higuchi Fractal Dimension (HFD), Hjorth Parameters, Spectral Entropy parameters, Spectral Entropy (SE), in which the amount of entropy in the spectral domain is calculated using relative intensity ratio (RIR) of the power spectral density (PSD) of the signal as scalar feature, and a Singular Value Decomposition (SVD) entropy, which is a dictionary type of analysis where the signal is decomposed based on a dictionary and the signal can be represented by a linear sum of the dictionary component.

One example of a connectivity feature includes a neuronal oscillatory synchronization, which refers to the presence of some type of fixed relationship among oscillatory modulations in neural activity based on different neurons or a group of neurons. The phase synchronization of these oscillatory neurons or group of neurons, particularly temporal and spatial frequency abnormalities in the phase synchronization, can be quantified, using frequency band phase synchronization approach to the multichannel EEG signals. Specifically, a difference in the phase, $\Delta\Phi_{xy}(t)$, between the two signals from two electrodes, x and y, is defined as $\Phi_y(t)-\Phi_y(t)$. An frequency band phase synchronization feature for two electrodes, $BS_{xy}$ can be calculated as the magnitude sum of the differences of phase between across a defined epoch for a given frequency band (e.g., alpha, beta, gamma, delta, or theta), such that:

$$BS_{xy} = \frac{1}{N}\left\|\sum\nolimits_{t=1}^{N} e^{j(\Delta\Phi_{xy}(t))}\right\| \quad \text{Eq. 1}$$

wherein N is a number of samples in the defined epoch.

While a phase synchronization feature can be calculated for each possible pair of electrodes across each frequency band, it will be appreciated that the potential number of features is large. In a system using thirty-two electrodes, such as a standard 10-20 arrangement, nearly five-hundred pairs will be available for each frequency band. Accordingly, in one implementation, the feature set can be reduced to a number of pairs most relevant to the classification.

The signal decomposition features can include signals derived via a principle component analysis, an Empirical Mode decomposition, a discrete wavelet transform, or similar processes. Time and frequency features can be determined as coefficients from a discrete Fourier transform, autoregressive methods, or a continuous wavelet transform. In one implementation, in which a wavelet decomposition is used, the signal decomposition features include a scale-dependent and scale-invariant feature for each electrode. For a time series of voltage values from an $i^{th}$ electrode, $x_i$, the wavelet coefficients, $W_a(n)$, produced in a wavelet decomposition can be defined as:

$$W_a(n) = a^{-1}\sum_{i=1}^{M} x_i\psi\left(\frac{i-n}{a}\right) \quad \text{Eq. 2}$$

wherein ψ is the wavelet function, M is the length of the time series, and a and n define the coefficient computation locations.

a Scale-Dependent Feature, SD, can be Determined as:

$$SD = \sqrt{\frac{1}{N-1}\sum_{j=1}^{N}(W_a(n) - W_a)} \quad \text{Eq. 3}$$

wherein N=M/a is the number of coefficients at a given scale, a, and $W_a$ is a mother wavelet function.

The scale-independent feature, SI, can be calculated as the sum of the $q^{th}$ powers of the maxima of the wavelet function in Eq. 3, and represents different fractal properties of the time series of voltage values at different scaling components, τ(q), such that:

$$SI = \sum_i \|W_a(i)\|^2 \sim a^{\tau(q)} \quad \text{Eq. 4}$$

It will be appreciated that the specific wavelet function, the scale, a, and the value for q can vary with the application. In one example, a Morlet function can be used.

Autoregression features are derived via a spectral analysis model in which the voltage values of each electrode, x(n), are modelled as the output of a linear system characterized by a rational structure. A set of parameters are estimated from a given data sequence x(n), where 0<=n<=N−1, from which the power spectral density (PSD) is computed. The PSD can be computed by solving a series of linear equations whereby the data is modeled as an output of causal, all-pole, discrete filters whose input is white noise. The autoregression model for each electrode, with order p, can be expressed as:

$$x(n) = -\sum_{k=1}^{p} a(k)x(n-k) + w(n) \quad \text{Eq. 5}$$

wherein a(k) are the p autoregression coefficients, and w(n) is a white noise signal having a variance equal to that of the signal, x(n).

In one implementation, the autocorrelation function is determined via the Burg method, with an appropriate order, p, for the autocorrelation selected according to the Akaike information criterion (AIC). Rather than using the entire spectrum as a feature, six different types of features can be extracted from each of the five main frequency ranges used in EEG analysis, alpha, beta, gamma, delta, and theta. The features can include: 1) a mean power of each frequency range; 2) a variance power of each frequency range; 3) a mean frequency of the observed mean power in each frequency range; 4) a variance frequency of the observed mean power in each frequency range, and the ratio between; 5) a mean power for each frequency range; and 6) a variance for each frequency range. It will be appreciated, however, that other descriptive statistics representing the frequency content of the signal can also be utilized.

In another implementation, the classification features can be a change in two or more of the features described above between a first EEG, taken at a first time, and a second EEG, taken at a second time. This allows for monitoring of a change in the subject's condition over time, for example, in response to treatment. In another example, the classification features can include a derivative of one or more of the features with respective to time to track the rate of change in the feature over time. In some implementations, higher derivatives with respect to time can also be used as features.

The feature reduction process 234 generates composite features from the plurality of extracted features to reduce the dimensionality of the feature space for classification. Appropriate composite features can be generated via feature reduction algorithms, such as Lasso, ElasticNet, Randomized PCA, ISO MAP, SPECTRAL Embedding, Random Projections, Tree Based Methods, Recursive Feature Selection, and Multivariate feature reduction. In one implementation, a univariate method, such as a mutual information measure, is employed to identify features that are substantially independent for use in the classifier. These features can be combined as a linear combination with weighted terms to form a composite feature, which can then be used for classification. Alternatively or additionally, a principle component analysis can be employed to generate a set of composite features for classification from the extracted features. This reduces the complexity of the classifier and reduces the likelihood of overfitting the classifier to the known training samples.

A pattern recognition classifier 238 uses the generated composite features to classify a subject into one of a plurality of classes, each representing one of the presence of a pain disorder generally or a specific pain disorder (e.g., fibromyalgia), a type of pain, a symptom or finding from a physical exam associated with a pain disorder, a subtype of a pain disorder, a severity of pain, a severity of a pain disorder, a presence or absence of a pain phenomenon, a response to treatment for a pain disorder, a change in the patient's condition, a presence or absence of a given tender spot, and a likelihood that the subject suffers from a pain disorder generally or a specific pain disorder, according to the composite features. In one implementation, the classification is binary, with "pain disorder" and "non-pain disorder" classes, although it will be appreciated that additional classes could be included, for example, classes representing ranges of likelihoods that the subject suffers from a pain disorder. In another implementation, the classes could represent a subject's change in condition, with or without treatment, for example, "improving", "no change", and "degrading" classes, or classes representing degrees of change.

It will be appreciated that features from the original extracted features, as well as other clinical data representing the patent, can be used in addition to the composite features. Clinical parameters can include, but are not limited to demographic parameters (e.g., age, sex), physiological parameters (blood pressure, blood glucose, heart rate, oxygen saturation, etc.), a medical history of the subject, including, for example, categorical variables representing the presence or absence of various conditions, and medications taken by the subject, as well as respective dosages for these medications.

The pattern recognition classifier 238 can utilize one or more pattern recognition algorithms, each of which analyze the extracted features or a subset of the extracted features to classify the subjects into one of the plurality of classes and provide this information to a display 240. Where multiple classification or regression models are used, an arbitration element can be utilized to provide a coherent result from the plurality of models. The training process of a given classifier will vary with its implementation, but training generally involves a statistical aggregation of training data into one or more parameters associated with the output class. The training process can be accomplished on a remote system and/or on the local device or wearable, app. For rule-based models, such as decision trees, domain knowledge, for example, as provided by one or more human experts, can be used in place of or to supplement training data in selecting rules for classifying a user using the extracted features. Any of a variety of techniques can be utilized for the classification algorithm, including support vector machines (SVMs), regression models, self-organized maps, fuzzy logic systems, data fusion processes, boosting and bagging methods, rule-based systems, or artificial neural networks (ANNs).

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. In one implementation, the SVM can be implemented via a kernel method using a linear or non-linear kernel.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

Many ANN classifiers are fully-connected and feedforward. A convolutional neural network, however, includes convolutional layers in which nodes from a previous layer are only connected to a subset of the nodes in the convolutional layer. Recurrent neural networks are a class of neural networks in which connections between nodes form a directed graph along a temporal sequence. Unlike a feedforward network, recurrent neural networks can incorporate feedback from states caused by earlier inputs, such that an output of the recurrent neural network for a given input can be a function of not only the input but one or more previous inputs. As an example, Long Short-Term Memory (LSTM) networks are a modified version of recurrent neural networks, which makes it easier to remember past data in memory.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used.

In one example, an unsupervised machine learning model can be applied using the extracted features. In this instance, the identity and number of categories into which a subject can be assigned is not known a priori. For example, research on new types and subtypes of pain disorders might utilize an unsupervised learning process to identify sets of subjects having similar characteristics or that deviate from expected parameters. Examples of unsupervised learning algorithms that could be used for this purpose include clustering algorithms, such as k-means and hierarchical clustering, self-organized maps, and anomaly detection systems.

Figure 3:
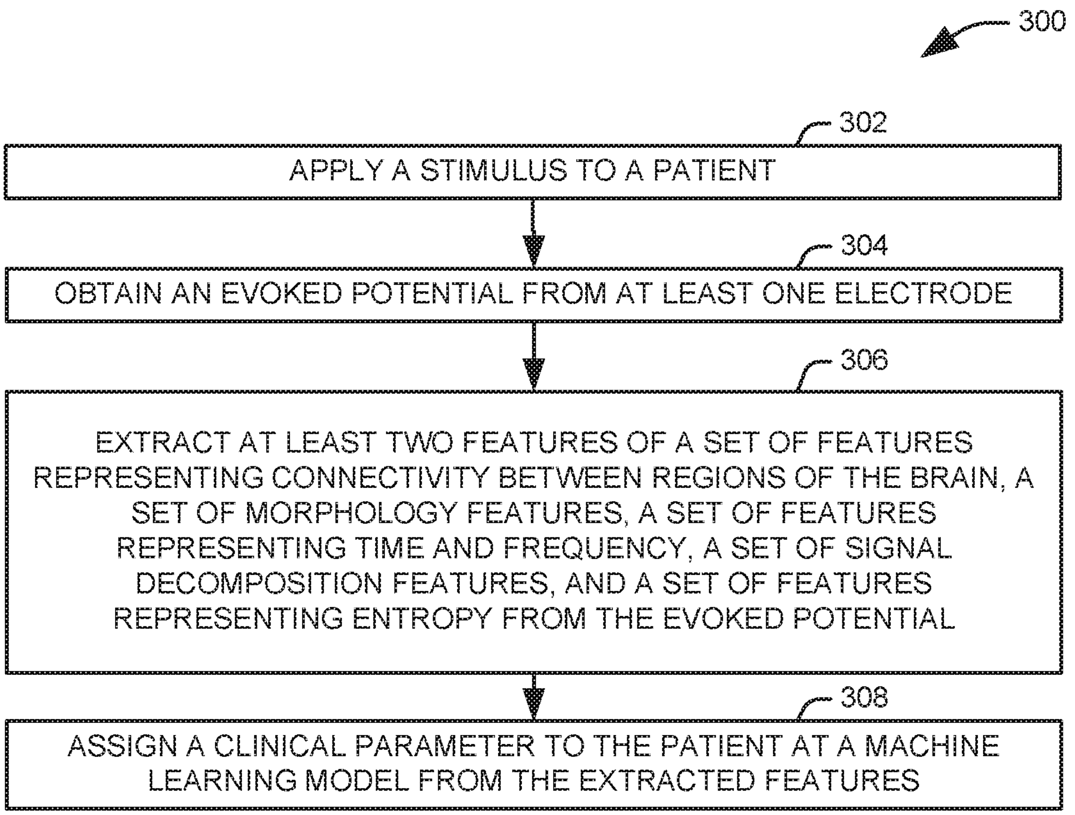
FIG. 3 illustrates one example of a method for diagnosing pain disorders.
Figure 4:
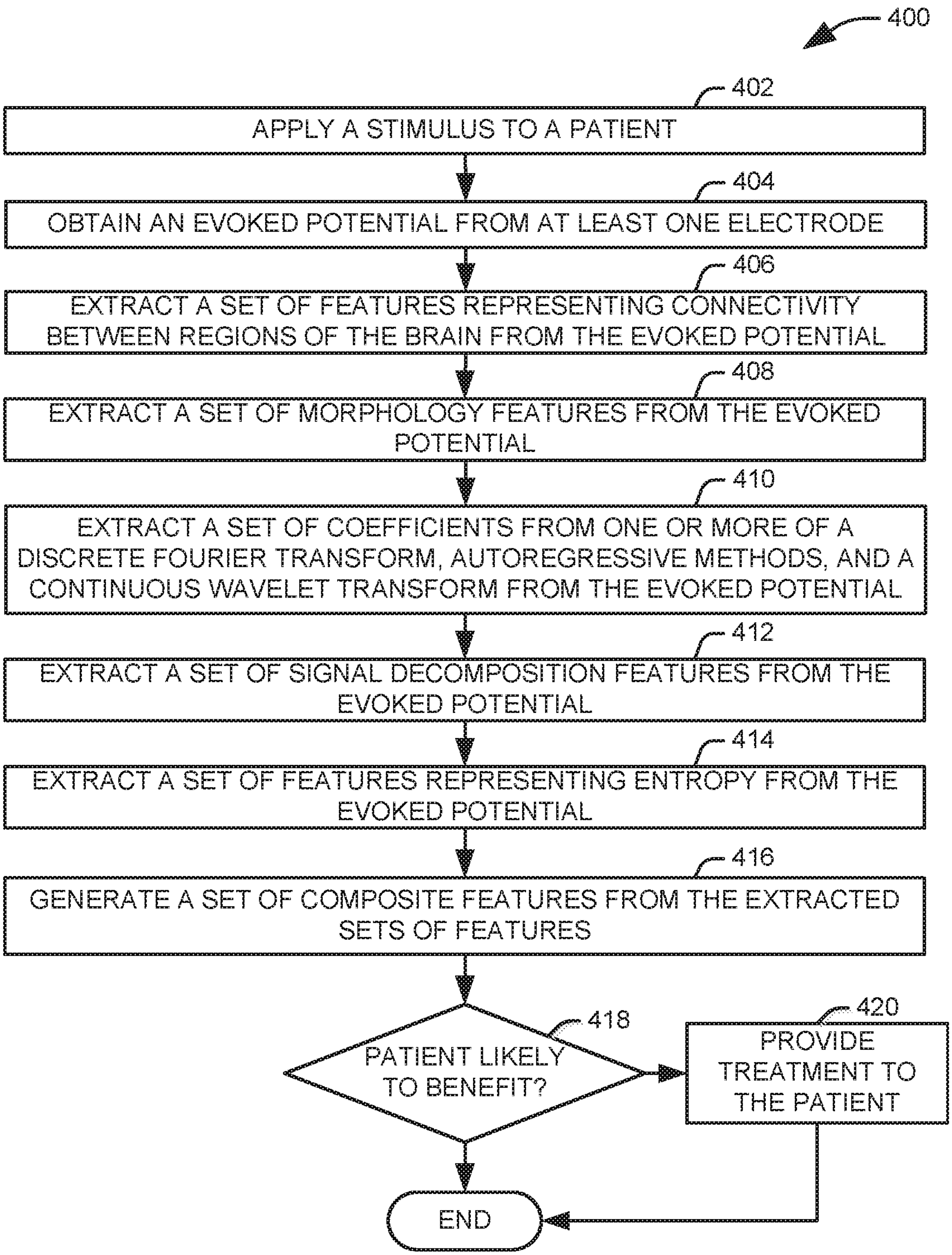
FIG. 4 illustrates one example of a method for determining if a subject is likely to respond to treatment.

In view of the foregoing structural and functional features described above, example methods will be better appreciated with reference to FIGS. 3 and 4. While, for purposes of simplicity of explanation, the example method of FIGS. 3 and 4 is shown and described as executing serially, it is to be understood and appreciated that the present examples are not limited by the illustrated order, as some actions could in other examples occur in different orders, multiple times and/or concurrently from that shown and described herein. Moreover, it is not necessary that all described actions be performed to implement a method.

FIG. 3 illustrates one example of a method 300 for diagnosing pain disorders. At 302, a stimulus is applied to the subject. At 304, at least one electrogram of a subject is obtained to provide an evoked potential. It will be appreciated that where multiple electrograms are taken, the stimulus of 302 can precede each electrogram. The electrogram includes a plurality of electrogram signals, each taken from an electrode placed on the scalp of the subject. In one example, multiple electrogram s can be taken to provide a plurality of event related potentials in response to applied stimuli, which are then averaged to isolate an event related potential.

At 306, a set of features are extracted from the evoked potential, including features from at least two of a set of features representing connectivity between regions of the brain, a set of morphology features, a set of features representing time and frequency, as a set of signal decomposition features, and a set of features representing entropy. In one implementation, features of all five types are extracted. The set of morphology features can include, for example, any or all of an amplitude of an N1 peak in the evoked potential, a depth of the N1 peak in the evoked potential, an amplitude of a P1 trough in the evoked potential, a depth of the P1 trough in the evoked potential, a peak to peak voltage, and a duration of the event related potential. The set of features representing entropy can include any or all of a Petrosian fractal dimension, a Higuchi fractal dimension, Hjorth parameters, spectral entropy parameters, and a singular value decomposition entropy.

The set of signal decomposition features can include values derived via one of a principle component analysis, an empirical mode decomposition, and a discrete wavelet transform. The set of features representing time and frequency can include coefficients from one of a discrete Fourier transform, autoregressive methods, and a continuous wavelet transform. The set of features representing connectivity between regions of the brain can include measures of neuronal oscillatory synchronization, as have been described previously. In one implementation, the extracted set of features can be combined, for example, in accordance with a feature reduction algorithm applied during training of a machine learning model, to provide a set of composite features as part or all of the extracted set of features.

At 308, a clinical parameter relating to a pain disorder is assigned to the subject from the extracted set of features at a machine learning model. By "relating to a pain disorder," it is meant that clinical parameter represents any of the presence of a pain disorder generally or a specific pain disorder; a predicted or actual change in the subject's condition a pain disorder, a presence or absence of a given tender spot, a type of pain, a subtype of a pain disorder, a severity of pain, a severity of a pain disorder, the presence of absence of a particular pain phenomena, an intensity of a particular pain phenomena, a likelihood that the subject suffers from a pain disorder generally, or a likelihood that the subject suffers from a specific pain disorder. In one example, the subject is classified into one of a plurality of classes according to the extracted features, for example, via a support vector machine or random forest classifier trained on known training samples taken from subjects whose associated class is known. If it is determined that the subject will benefit from treatment, treatment can be provided, such as behavioral biofeedback, psychotherapy, (e.g., cognitive behavioral therapy), focused on addressing sleep disorders, training in relaxation techniques, and pharmaceutical interventions.

FIG. 4 illustrates one example of a method 400 for determining if a subject is likely to respond to treatment in accordance with an aspect of the present invention. At 402, a stimulus is applied to the subject. At 404, an evoked potential is obtained from at least one electroencephalogram (EEG) of the subject. In one implementation, a plurality of event related potentials are obtained from the subject in response to respective stimuli, and the evoked potential is generated as a Woody Filter Mean across the plurality of event related potentials.

At 406, a set of features representing connectivity between regions of the brain is extracted from the evoked potential. At 408, a set of morphology features is extracted from the evoked potential. At 410, a set of coefficients from one of a discrete Fourier transform, autoregressive methods, and a continuous wavelet transform is extracted from the evoked potential. At 412, a set of signal decomposition features is extracted from the evoked potential. At 414, a set of features representing entropy is extracted from the evoked potential. At 416, each of the set of features representing connectivity between regions of the brain, the set of morphology features, the set of coefficients from the one of the discrete Fourier transform, autoregressive methods, and the continuous wavelet transform, the set of signal decomposition features, and the set of features representing entropy are combined to provide a set of composite features. It will be appreciated that an appropriate feature reduction algorithm can be applied during training of a machine learning model to determine appropriate composite features for the analysis.

At 418, it is determined if the subject is likely to benefit from a treatment to a pain disorder from the set of composite features at a machine learning model. It will be appreciated that the machine learning model can provide an output representing whether the subject has or likely has a pain disorder, determining if a certain treatment is likely to be successful, or if a treatment that is currently in progress is effective at treating the pain disorder. If it is determined that the treatment is unlikely to benefit the subject (N), the method terminates. Otherwise (Y), the treatment is provided to the subject at 420. In the illustrated example, the treatment can include behavioral biofeedback, psychotherapy, training in relaxation techniques, and/or pharmaceutical interventions.

Figure 5:
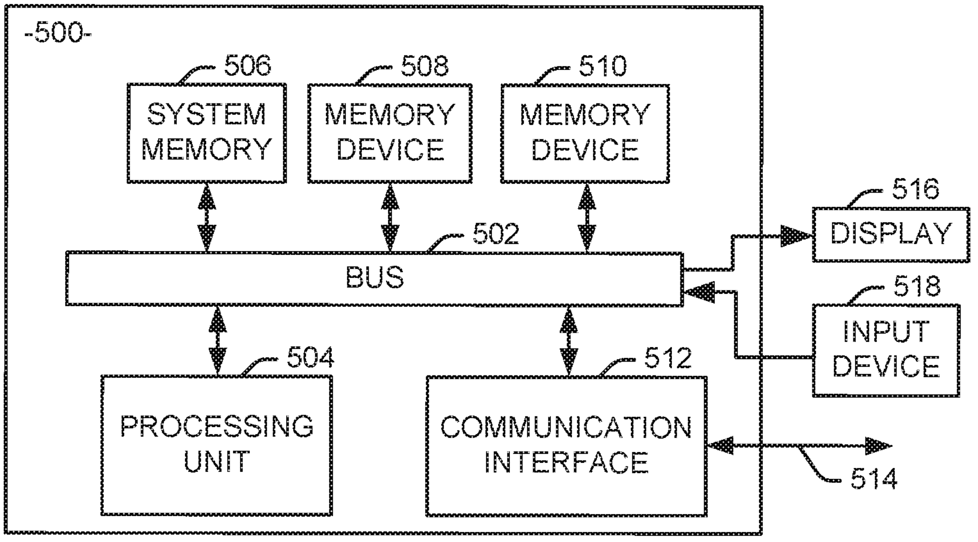
FIG. 5 is a schematic block diagram illustrating an exemplary system of hardware components.

FIG. 5 is a schematic block diagram illustrating an exemplary system 500 of hardware components capable of implementing examples of the systems and methods disclosed herein. The system 500 can include various systems and subsystems. The system 500 can be a personal computer, a laptop computer, a workstation, a computer system, an appliance, an application-specific integrated circuit (ASIC), a server, a server BladeCenter, a server farm, etc.

The system 500 can include a system bus 502, a processing unit 504, a system memory 506, memory devices 508 and 510, a communication interface 512 (e.g., a network interface), a communication link 514, a display 516 (e.g., a video screen), and an input device 518 (e.g., a keyboard, touch screen, and/or a mouse). The system bus 502 can be in communication with the processing unit 504 and the system memory 506. The additional memory devices 508 and 510, such as a hard disk drive, server, standalone database, or other non-volatile memory, can also be in communication with the system bus 502. The system bus 502 interconnects the processing unit 504, the memory devices 506-510, the communication interface 512, the display 516, and the input device 518. In some examples, the system bus 502 also interconnects an additional port (not shown), such as a universal serial bus (USB) port.

The processing unit 504 can be a computing device and can include an application-specific integrated circuit (ASIC). The processing unit 504 executes a set of instructions to implement the operations of examples disclosed herein. The processing unit can include a processing core.

The additional memory devices 506, 508, and 510 can store data, programs, instructions, database queries in text or compiled form, and any other information that may be needed to operate a computer. The memories 506, 508 and 510 can be implemented as computer-readable media (integrated or removable), such as a memory card, disk drive, compact disk (CD), or server accessible over a network. In certain examples, the memories 506, 508 and 510 can comprise text, images, video, and/or audio, portions of which can be available in formats comprehensible to human beings.

Additionally or alternatively, the system 500 can access an external data source or query source through the communication interface 512, which can communicate with the system bus 502 and the communication link 514.

In operation, the system 500 can be used to implement one or more parts of a pain evaluation system in accordance with the present invention, in particular, the feature extractor 104 and the machine learning model 106. Computer executable logic for implementing the pain evaluation system resides on one or more of the system memory 506, and the memory devices 508 and 510 in accordance with certain examples. The processing unit 504 executes one or more computer executable instructions originating from the system memory 506 and the memory devices 508 and 510. The term "computer readable medium" as used herein refers to a medium that participates in providing instructions to the processing unit 504 for execution. This medium may be distributed across multiple discrete assemblies all operatively connected to a common processor or set of related processors.

Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A method for diagnosing a mechanical pain disorder comprising:

applying a stimulus to a subject, the stimulus being associated with the mechanical pain disorder;

obtaining an evoked potential from at least one electrogram of the subject;

extracting a set of features from the evoked potential including features from at least two of a set of features representing connectivity between regions of the brain, a set of morphology features, a set of features representing time and frequency, a set of signal decomposition features, and a set of features representing entropy; and classifying the subject into one of a first class, representing the presence of the mechanical pain disorder, and a second class, representing the absence of the mechanical pain disorder, using the extracted set of features with a machine learning model trained on known training samples taken from a set of subjects whose associated class is known, the set of subjects including subjects belonging to each of the first class and the second class.

2. The method of claim 1, wherein the set of features representing entropy comprise a Petrosian fractal dimension, a Higuchi fractal dimension, Hjorth parameters, spectral entropy parameters, and a singular value decomposition entropy.

3. The method of claim 1, wherein the set of signal decomposition features include values derived via one of a principle component analysis, an empirical mode decomposition, and a discrete wavelet transform.

4. The method of claim 1, wherein the set of features representing connectivity between regions of the brain includes a measure of neuronal oscillatory synchronization.

5. The method of claim 1, further comprising combining the extracted set of features to provide a set of composite features, wherein classifying the subject into one of the first class and the second class with the machine learning model according to the extracted set of features comprises classifying the subject into one of the first class and the second class at the machine learning model according to the set of composite features.

6. The method of claim 1, wherein applying the stimulus to the subject and obtaining the evoked potential from the at least one electrogram of a subject comprises:

applying a first stimulus to the subject;

obtaining a first event related potential from the at least one electrogram after the first stimulus is applied;

applying a second stimulus to the subject;

obtaining a second event related potential from the at least one electrogram after the second stimulus is applied; and averaging at least the first event related potential and the second event related potential to provide the evoked potential.

7. The method of claim 1, further comprising providing treatment to the subject if the subject is classified into the first class, the treatment comprising one of behavioral biofeedback, training in relaxation techniques, psychotherapy, and pharmaceutical interventions.

8. The method of claim 1, wherein the stimulus is a first stimulus, the evoked potential is a first evoked potential, and the electrogram is a first electrogram taken at a first time, the method further comprising applying a second stimulus to a subject at a second time and obtaining a second evoked potential from a second electrogram of the subject, wherein the set of features represent changes in features from at least two of the set of features representing connectivity between regions of the brain, the set of morphology features, the set of features representing time and frequency, the set of signal decomposition features, and the set of features representing entropy.

9. The method of claim 1, wherein applying a stimulus to the subject comprises applying mechanical pressure to a selected location on the body of the subject.

10. A system for diagnosing a mechanical pain disorder comprising:

a processor; and a non-transitory computer readable medium, operably connected to the processor, that stores machine readable instructions that are executed by the processor to provide:

an electrogram interface that receives a recorded evoked potential from an electrogram of a subject, the evoked potential being recorded in response to a stimulus associated with a mechanical pain disorder;

a feature extractor that extracts a set of features from the evoked potential including features from at least two of a set of features representing connectivity between regions of the brain, a set of morphology features, a set of features representing time and frequency, a set of signal decomposition features, and a set of features representing entropy; and a machine learning model trained on a set of training samples that each include values for the set of features and a value for the clinical parameter from a set of subjects having a known value for the clinical parameter, that assigns a clinical parameter to the subject from the extracted set of features, the clinical parameter assuming either a first value, representing the presence of the mechanical pain disorder and a second value, representing the absence of the mechanical pain disorder, the set of subjects including subjects having each of the first value for the clinical parameter and the second value for the clinical parameter.

11. The system of claim 10, further comprising:

a set of electrodes that provides the electrogram of the subject to the electrogram interface; and an output device that provides the clinical parameter to a user.

12. The system of claim 10, wherein the set of features includes features from each of the set of features representing connectivity between regions of the brain, the set of morphology features, the set of features representing time and frequency, the set of signal decomposition features, and the set of features representing entropy.

13. The system of claim 10, wherein the set of features representing time and frequency comprise coefficients from one of a discrete Fourier transform, autoregressive methods, and a continuous wavelet transform.

14. The system of claim 10, wherein the machine learning model comprises one of a support vector machine and a random forest classifier.

15. The system of claim 10, further comprising a feature reduction component that combines the extracted set of features to provide a set of composite features, the machine learning model assigning the clinical parameter to the subject according to the set of composite features.

16. A method for evaluating a pain disorder comprising:

applying a stimulus to a subject;

obtaining an evoked potential from at least one electrogram of the subject;

extracting a set of features from the evoked potential including features from a set of features representing entropy and at least one of a set of features representing connectivity between regions of the brain, a set of morphology features, a set of features representing time and frequency, and a set of signal decomposition features, the set of features representing entropy comprising a Petrosian fractal dimension, a Higuchi fractal dimension, Hjorth parameters, spectral entropy parameters, and a singular value decomposition entropy; and classifying the subject into one of a first class, representing the presence of the pain disorder, and a second class, representing the absence of the pain disorder, using the extracted set of features with a machine learning model trained on known training samples taken from subjects whose associated class is known.

* * * * *